United States Patent [19]
Choromokos

[11] Patent Number: 5,211,171
[45] Date of Patent: May 18, 1993

[54] PORTABLE LUNG PURGER AND VENTILATOR SYSTEM

[76] Inventor: Robert Choromokos, 7712 Palacio Dr., San Diego, Calif. 92127

[21] Appl. No.: 830,372

[22] Filed: Jan. 31, 1992

[51] Int. Cl.⁵ ............................................ A61M 16/00
[52] U.S. Cl. ............................................. 128/205.19
[58] Field of Search ................ 128/205.19, 205.18, 128/205.12, 205.24

[56] References Cited

U.S. PATENT DOCUMENTS

| | | | |
|---|---|---|---|
| 3,461,866 | 8/1969 | Ritchie | 128/205.18 |
| 4,289,126 | 9/1981 | Sierig et al. | 128/205.19 X |
| 4,941,469 | 7/1990 | Adahan | 128/205.18 |
| 5,044,362 | 9/1991 | Younes | 128/205.18 X |

*Primary Examiner*—William H. Grieb
*Attorney, Agent, or Firm*—Baker, Maxham, Jester & Meador

[57] ABSTRACT

A portable lung purger and ventilator system for exhausting airborne contaminants from the lungs, includes a mouthpiece sized and configured for placement at an individual's mouth, the mouthpiece having an inlet for receiving a gas stream and an outlet for transferring a gas stream received through the inlet; a vacuum pump having an inlet in fluid communication with the mouthpiece for receiving a gas stream and an outlet for exhausting a gas stream received through the pump inlet, the vacuum pump generating a vacuum at the mouthpiece; a drive operatively connected with the vacuum pump for providing motive power thereto; a switch operatively connected with the drive for controlling operation thereof; a portable power source operatively connected with the drive for providing power thereto; and the mouthpiece, vacuum pump, drive, switch and power source being arranged in a portable assembly.

20 Claims, 8 Drawing Sheets

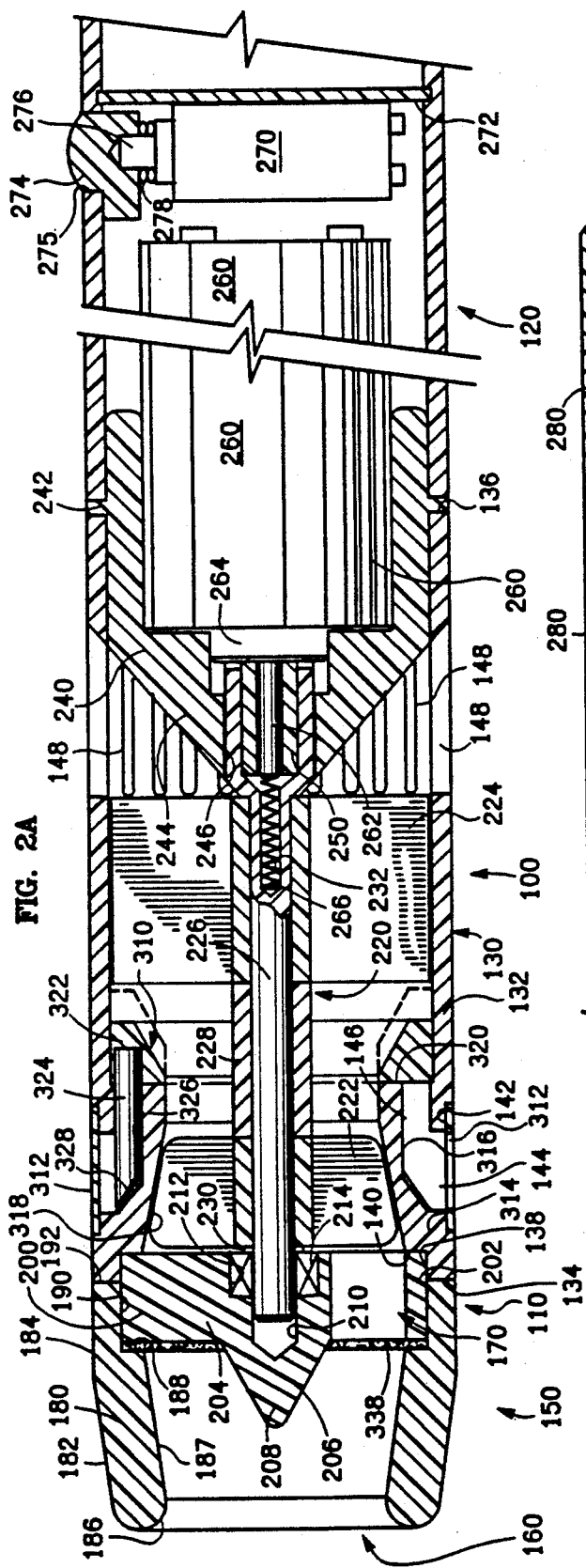
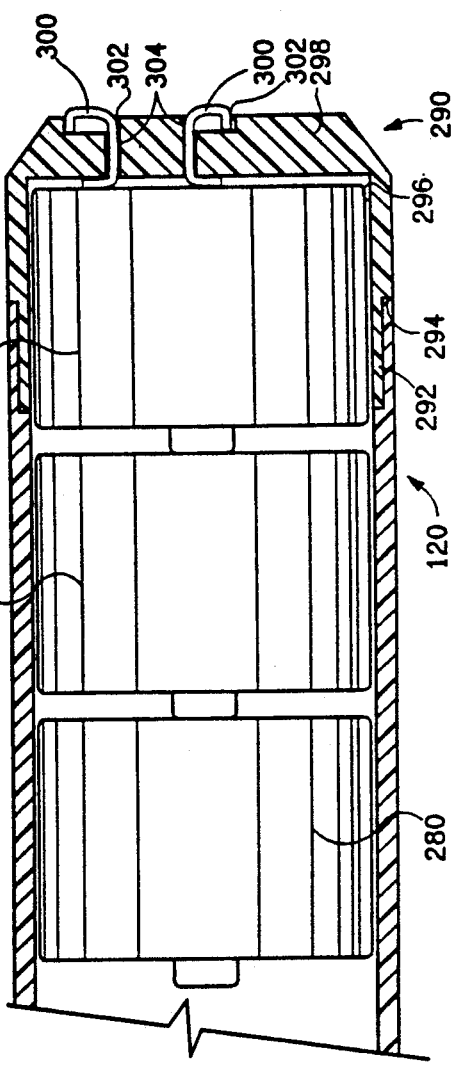
FIG. 2A
FIG. 2B

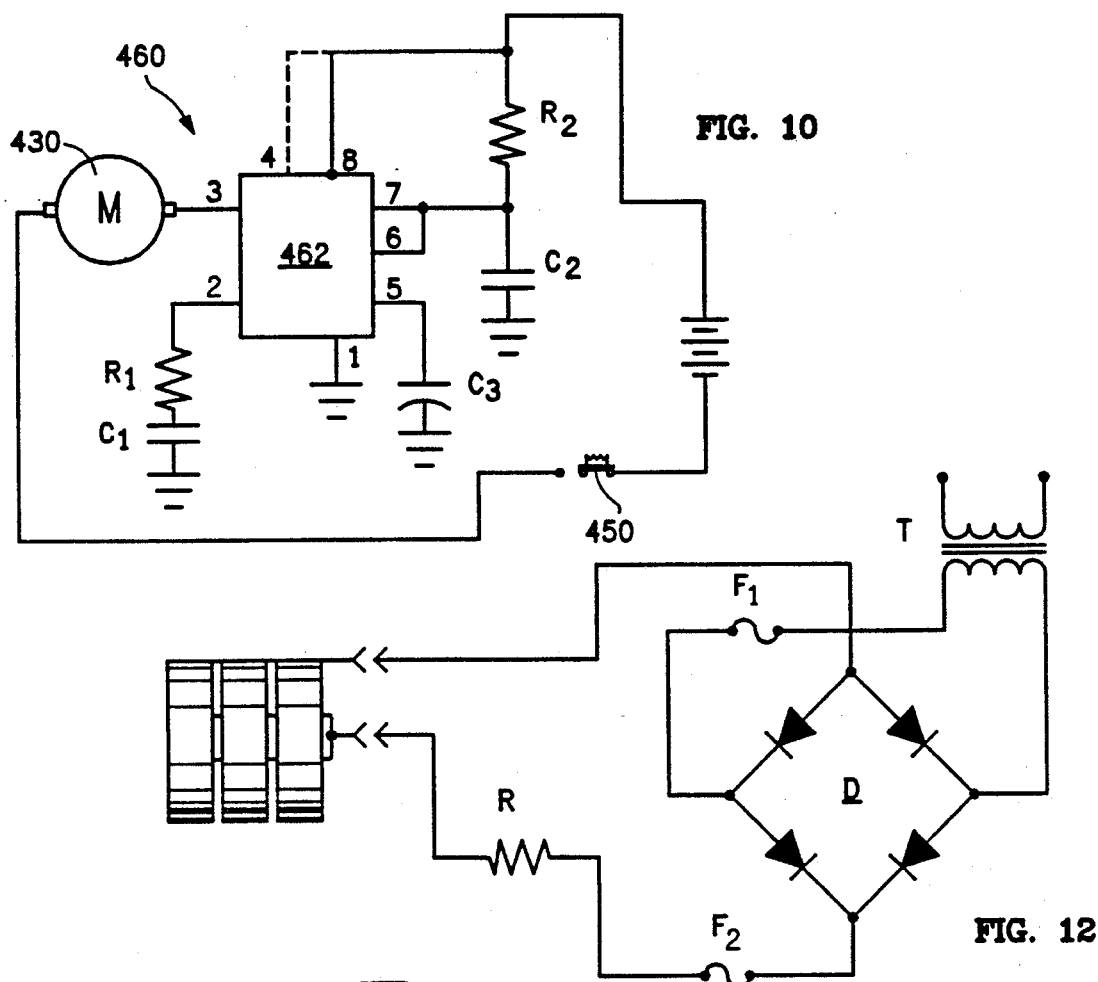
FIG. 10
FIG. 12
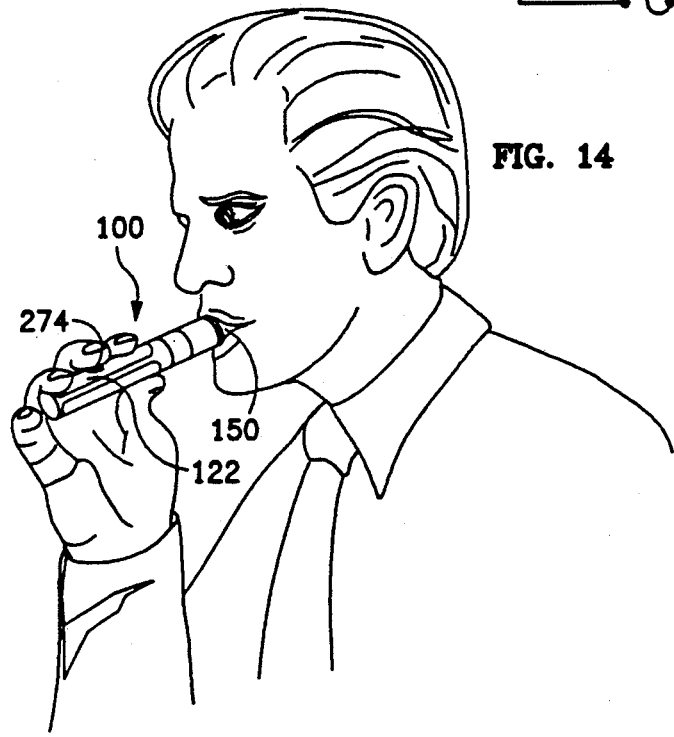
FIG. 14

PORTABLE LUNG PURGER AND VENTILATOR SYSTEM

BACKGROUND OF THE INVENTION

The present invention relates to pulmonary assistance apparatus. More particularly, the invention relates to a pulmonary cleansing system for countering the effects of unhealthful environmental conditions on the human pulmonary system and for relieving symptoms caused by chronic or transitory pulmonary conditions. Still more particularly, the invention relates to a potentially life-saving lung purging system for smokers which removes residual smoke from the lungs following inhalation and before such smoke has an opportunity to cause irreversible lung damage.

According to the Surgeon General, tobacco smoking is the chief avoidable cause of death in our society and the most important health issue of our time. It is estimated that at least 350,000 American deaths per year are attributable to smoking. This is more than the number of all other drug and alcohol abuse deaths combined, more than all automobile fatalities per year, more than the number of recorded deaths caused by AIDS (Acquired Immune Deficiency Syndrome), and more than all American military fatalities in World War I, World War II, and Vietnam put together. Secondary smoke inhaled by nonsmokers may be no less a health hazard. According to estimates, at least 100,000 people die every year due to the effects caused by secondary smoke inhalation.

There are an estimated 300 million cigarette smokers worldwide. Among this population, factors such as rate of consumption, brand preference, potency, etc., tend to vary by age, gender, culture and the like. Notwithstanding such differences, the smoking process itself and the resultant physiological effects, are fairly uniform throughout all smoker groups. In order to experience the full pleasures of smoking, cigarette smokers usually "inhale" tobacco smoke deep into the lungs. There, the smoke circulates and contacts the lung surfaces where nicotine and other constituents are absorbed into the bloodstream. Nonabsorbed materials such as tar tend to remain on and coat the lung tissue.

Due to limited available lung surface area, not all of the smoke-borne particulates ingested during a single cigarette inhale are immediately deposited on the lungs. If the lungs are forcefully evacuated following inhale, smoke will be visibly exhaled. In the case of most smokers, however, the force of an exhale almost never matches the depth of the inhale. As a result, a residuum of smoke drawn deep into the lungs during inhale tends to remain in the lungs even after subsequent exhale. This smoke may survive in the lungs despite many subsequent exhales. Indeed, upon the completion of smoking a cigarette, nonexhaled residual cigarette smoke can remain suspended in the lungs for approximately thirty minutes to one hour after inhalation, depending on such factors as lung capacity and respiratory rate during smoking. In the case of heavy smokers, this means that the smokers' lungs may never be cleared of smoke except during sleep. It is this residual smoke, and the particulates in the smoke, that slowly settles in the lungs and causes significant pulmonary damage.

The detrimental effects caused by the presence of residual contaminant-laden air in the lungs are not limited to persons exposed to primary and secondary smoke alone. In an increasing number of urban areas, the atmospheric environment in which the bulk of daily activity occurs is literally choked with a multitude of harmful contaminants. Substantial quantities of pollutants are emitted on a daily basis from automobiles, industrial and other sources. Such compounds include ozone, carbon monoxide, sulfur dioxide, nitrogen dioxide and lead, to name but a few.

In some areas, significant outdoor activity may actually be dangerous, and children, older individuals and persons with chronic pulmonary conditions may be advised to remain indoors. The long-term health effects of such environmental conditions have not been completely determined. However, the results of initial studies suggest at least a pronounced decrease in lung capacity among persons exposed to polluted air for long periods. It is also believed that air pollution may be a contributing cause of such health problems as emphysema, lung cancer, pulmonary dysfunction, chronic bronchitis, asthma and cardiovascular disease. Air pollution can also destroy the cilia (minute hairlike parts of cells) that line air passages of the body. The cilia trap germs and other particles before they have a chance to enter the lungs. If the cilia are damaged, these particles can build up in the lungs and increase vulnerability to disease. Individuals having preexisting respiratory ailments are generally most at risk.

An average adult individual takes approximately fifteen breaths per minute while at rest. At this rate, over a 24-hour period, the individual takes approximately 21,600 breaths. With each breath, millions of contaminant particles are ingested into the lungs. Those that are not expelled during subsequent exhale may ultimately be deposited on the lung tissue. The degree to which exhaling activity expels contaminants is a function of contaminant settling rate and the force of the exhale.

Each contaminant particulate has its own particular settling rate which is a function of its molecular mass. Lighter particles tend to remain airborne for longer periods and are more apt to be exhaled before settling. Heavier particles may settle very quickly on the lungs. As in the case of smokers, if contaminants are inhaled deeply into the lungs, the force of a subsequent exhale may not be sufficient to completely expel the contaminants. This results in a longer residency time and increases the number of contaminant particles likely to settle on the lungs. Because exhaling activity may never fully evacuate contaminants in the lungs, breathing pollutant-laden air for even relatively short periods can enable at least some contaminants to settle on the lung tissue. In areas having significant air pollution levels, the build-up of contaminants on lung tissue may be substantial. Short of periodically purging the lungs, for example, by intense exercise or consciously contracting the diaphragm, practical solutions to the problem of residual contaminant removal have not been forthcoming. Accordingly, an evident need exists for a system for safely and effectively treating the human respiratory system following ingestion of harmful pollutants such as smoke and other contaminants. Such apparatus should preferably remove contaminants ingested deep in the lungs that would not be otherwise removed by subsequent normal exhale, and which could therefore permanently settle on lung tissue and cause irreversible damage. Preferably, such apparatus would also include an ability to free recently deposited contaminants from the lung surfaces. In addition, such apparatus should be portable, compact, and self-operable. It is believed that further advantage could be derived by providing a lung ventilation capability to provide relief from lung swelling and congestion caused by ingestion of bacteria and viruses. In addition, many individuals could benefit from an apparatus to introduce medicament, such as asthma relief formulations, deep into the lungs.

SUMMARY OF THE INVENTION

The present invention is directed to a portable lung purger and ventilator system for assisting the removal of airborne contaminants from, and providing relief to the lungs. In preferred embodiments, the system includes a mouthpiece sized and configured for placement at an individual's mouth, the mouthpiece having an inlet for receiving a gas stream and an outlet for transferring a gas stream received through the inlet. A vacuum pump includes an inlet in fluid communication with the mouthpiece for receiving a gas stream and an outlet for exhausting a gas stream received through the pump inlet, the vacuum pump generating a vacuum at the mouthpiece. A drive is operatively connected with the vacuum pump for providing motive power thereto, and a switch is operatively connected with the drive for controlling operation thereof. A portable power source is further provided to provide power to the drive, and the mouthpiece, vacuum pump, drive, switch and power source are arranged in a portable assembly. In further embodiments, a vacuum pulsing system may be provided, as well as a system for introducing treated air or medicament into the lungs.

The lung purger and ventilator system has a wide range of applications, but is particularly advantageous to smokers. Daily use of the lung purger system will increase the number of total volumn air changes that the lungs would normally experience in the course of a day. Low activity people require fewer air changes than high activity persons. Increasing the respiratory rate by running, exercizing, etc. has been proven to be healthy. Therefor, if an average person's lungs have twenty complete "air changes" in an eight hour period, increasing the number of air changes with the lung purger system in that eight hour period would lessen the amount of contaminate air that settled in the lungs during the same time period.

This is particularly true for smokers. As indicated, upon the completion of smoking a cigarette, the inhaled particulate matter contained in cigarette smoke remains in a somewhat transient state for approximately thirty minutes to an hour in the lungs. It is during this transient period that there exists an opportunity to expel the particulate matter from the lungs before it settles permanently and causes irreversible lung damage. The lung purger system assists in exchanging the volume of air in the lungs at an accelerated rate. This rapid exchange of air increases the expulsion of damaging particulate matter and thus prevents it from permenantly settling in the lungs. In addition, the system may be provided with a vacuum pulsing system to help free previously deposited particulate matter.

BRIEF DESCRIPTION OF THE DRAWINGS

FIG. 2A is a partial cross-sectional side view showing a first portion of a lung purger and ventilator system constructed in accordance with a further aspect of the present invention.

FIG. 2B is a partial cross-sectional side view showing a second portion of the lung purger and ventilator system of FIG. 2A.

FIG. 10 is a schematic diagram of a pulsing circuit for use in a lung purger and ventilator system of the present invention.

FIG. 11 is a perspective view of the lung purger and ventilator system of FIG. 2A including an end cap and recharging unit.

FIG. 12 is a schematic diagram of a battery recharging circuit utilized in the lung purger and ventilator system of FIG. 11.

FIG. 13 is a cross-sectional side view showing the mutual engagement of the recharging unit and lung purger and ventilator system of FIG. 11.

FIG. 14 is a diagrammatic perspective view showing a method of use of the lung purger and ventilator system of FIG. 11.

DESCRIPTION OF THE PREFERRED EMBODIMENTS

Figure 1:
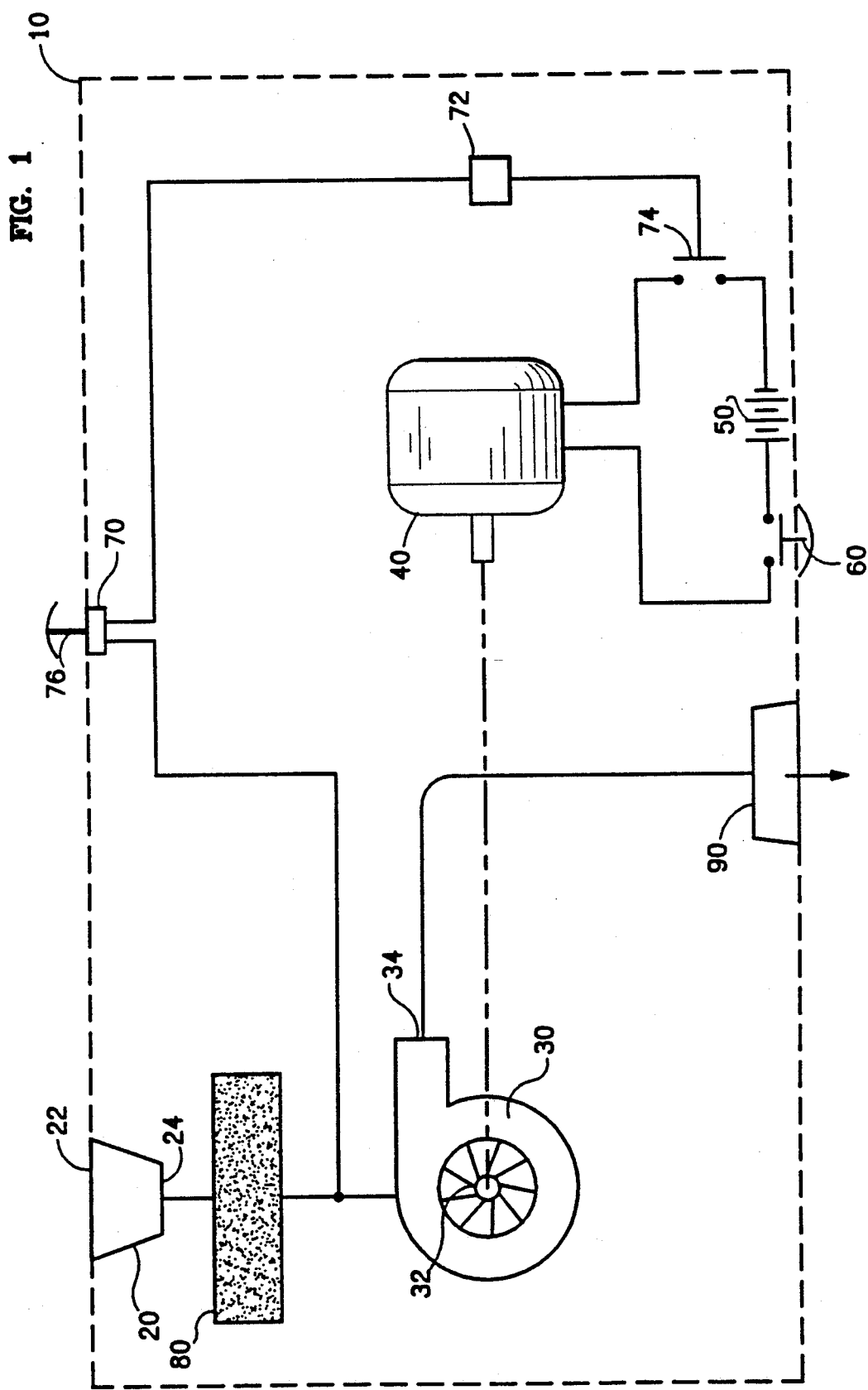
FIG. 1 is a diagrammatic illustration of a lung purger and ventilator system construction in accordance with one aspect of the present invention.

Referring now to FIG. 1, a portable lung purger and ventilator system includes an assembly 10 which is preferably portable and sized and configured to be handheld. The assembly 10 has disposed therein a mouthpiece 20 which is preferably sized and configured for placement in an individual's mouth, the mouthpiece having an inlet 22 for receiving a gas stream from the individual's mouth and an outlet 24 for transferring the gas stream received from the inlet 22. The portable assembly 10 further includes a vacuum pump 30, having a pump inlet 32 and a pump outlet 34. The pump inlet 32 is in fluid communication with the mouthpiece outlet 24 for receiving a gas stream therefrom. The vacuum pump 30 may be of any suitable type and would typically include one or more impeller stages having multiple impeller blades mounted on a common shaft which is rotated to generate a vacuum at the mouthpiece 20. Thus, the gas stream is drawn into the mouthpiece 20 and is exhausted through the pump outlet 34.

The vacuum pump 30 is driven by a drive motor 40 also disposed within the assembly 10. The motor 40 is operatively connected with the vacuum pump by an appropriate coupling system, such as a belt drive, a gear arrangement or a shaft drive. Preferably, the drive motor 40 is bidirectional so that the vacuum pump 30 can be operated in forward and reverse modes. The motor 40 is powered by a portable power source 50 which may include rechargeable batteries or the like. A pair of contacts 52 may be provided for electrical engagement with a recharging unit (not shown). The power source 50 is electrically connected to the drive motor 40 through a momentary switch 60 that is also disposed within the assembly 10.

The lung purger and ventilator system of FIG. 1 may further include a pressure relief valve 70 disposed within the assembly 10 on the vacuum side of the pump 30. The pressure relief valve 70 is adjusted to periodically open when a predetermined vacuum is generated by the vacuum pump 30 so as to purge the vacuum in the system. Thus, the pressure valve 70 functions as a vacuum pulsing system providing a pulsed vacuum at the mouthpiece 20. Optionally, the vacuum system 70 may be connected to a pressure sensitive switch 72 that is electrically connected to the power source 50 through a relay 74. In this arrangement, the pressure sensor 72 responds to excess system pressure to operate the relay 74 and interrupt power to the drive motor 40. When the pressure valve 70 is used to purge vacuum from the system, it may be connected to a vent 76 disposed in the portable assembly 10, which vent may include a system of louvered openings to assist in the vacuum purge.

There is also disposed in the portable assembly 10 a filter 80 for filtering particulate matter transported with a gas stream through the mouth piece 20. This prevents contaminants from being exhausted in the vicinity of an individual using the system. The filter 80 may be positioned where convenient in the assembly 10 for periodic removal and replacement. Thus, although the filter 80 is shown adjacent the mouthpiece 20, it could also be positioned at other locations in the vacuum line. As shown in FIG. 1, the gas stream introduced through the mouthpiece 20 is eventually dispensed through an exhaust 90, which may include an array of exhaust ports disposed in the portable assembly 10.

Referring now to FIGS. 2A and 2B, a lung purger and ventilator system is shown in a further aspect as including a case or housing 100. The case 100 is generally tubular in shape and is defined by a forward end section 110, a rearward end section 120, and a vacuum chamber housing 130 extending between the forward and rearward end sections 110 and 120. It is contemplated that each of these sections will be formed from durable plastic, although other materials such as aluminum may also be suitable. The case 100 is preferably sized and configured to be held in the palm of an individual's hand, as shown in more detail in FIG. 14. Thus, the case will typically have a length not in excess of about six inches and a diameter that does not exceed about one inch. Moreover, the rearward end section 120 provides a hand grip area which is comfortable for holding by an individual. In a preferred aspect, the hand grip area provided by the peripheral outer surface of the rearward end section 120 is polygonal in nature by virtue of the provision of a plurality of longitudinal depressions 122 formed in the otherwise cylindrical peripheral surface. Texturing or other gripping surfaces could also be provided.

The vacuum chamber housing 130 supports a pump including a two stage rotor assembly that assists in performing the operative lung purging functions of the system. The vacuum chamber housing 130 includes a generally cylindrical outer surface 132, an annular forward end 134 and an annular rearward end 136. The forward end 134 extends inwardly to a generally cylindrical inner surface 138 that extends rearwardly to an annular shoulder 140. The vacuum chamber housing 130 further includes an annular groove 142 disposed rearwardly of the annular shoulder 140. The annular groove 142 extends radially inwardly to an annular passage 144 to an interior vent chamber 146. Disposed forwardly of the rearward end 136 is a peripheral array of longitudinally extending vents 148 forming an exhaust outlet.

The case 100 further includes a mouthpiece 150 forming an extension at the forward end section 110. The mouthpiece 150 is slightly frustoconical, but generally tubular in shape and includes a generally circular inlet 160, a generally circular outlet 170 and a peripheral wall or barrel 180. In order to more suitably adapt the mouthpiece to the configuration of an individual's mouth, and thereby improve comfort, the mouthpiece barrel 180 has a forward outer surface 182 tapering gently outwardly as it extends from the inlet 160. The tapered outer surface 182 transitions at its rearward extent to a non-tapered generally cylindrical outer surface portion 184. The barrel 180 further includes a generally circular forward rounded end 186 forming the inlet 160. On the interior side of the barrel 180, an aprodynamically smooth interior surface 187 tapers outwardly from the forward end 184 to an annular shoulder 188. The annular shoulder 188 extends radially outwardly to a rearward, generally cylindrical interior surface 190 extending to a rear annular face 192. The rear face 192 intersects the outer surface portion 184 and defines the rearward extent of the forward end section 110.

Seated adjacent the shoulder 188 and engaging the inner surface 190 in a slideable, removable relationship, is a forward bearing support 200. Alternatively, these components could be removably joined by a threaded connection. The forward bearing support 200 may be made from any suitable plastic material, and includes an annular outer wall 202 which is also engaged in a press-fit relationship with the cylindrical inner surface 138 and annular shoulder 140 of the vacuum chamber housing 130. Preferably, the bearing support is permanently bonded to the vacuum chamber housing 130 by glue or other suitable attachment arrangements. It would also be possible to removably mount these components by providing a slideable or threaded connection therebetween. Thus, the pump chamber housing 130 and the forward end section 110 are joined together by mutual engagement with the forward bearing support 200. Preferably, the forward end section 110 may be readily removed by pulling it away from the bearing support 200. The vacuum chamber housing 130, however, would not normally be removable from the bearing support 200, unless provision for access to the interior of the vacuum chamber housing 130 was desired.

Figure 4:
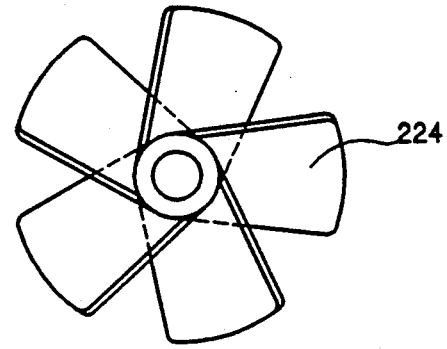
FIG. 4 is an end view of a secondary pump impeller of the lung purger and ventilator system of FIG. 2A.

As also shown in FIG. 4, the forward bearing support 200 further includes a pair of tangential, inwardly extending flanges 204 supporting a central hub 206. The central hub 206 includes an aerodynamically tapered nose cone section 208. Disposed in the central hub 206 is a shaft receptacle 210 and a bearing support well 212. Disposed within the bearing support well 212 is a roller bearing 214 of conventional design.

Figure 3:
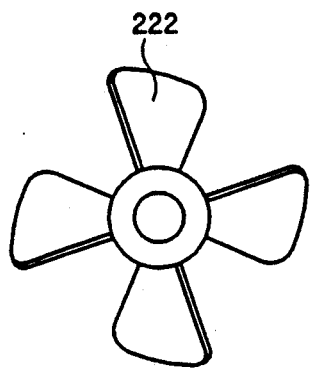
FIG. 3 is an end view of a primary pump impeller of the lung purger and ventilator system of FIG. 2A.

The vacuum chamber housing 130 has mounted therein a two stage vacuum pump 220 including a forward primary impeller 222 and a rearward secondary impeller 224 mounted on a common drive shaft 226. Both impellers 222, 224, and the shaft 226 are preferably made from durable plastic material. The forward impeller 222 serves as the primary airflow source whereas the rearward impeller 224 serves mainly to create the vacuum required for flow and vacuum purge valve pulsing, as will be discussed in more detail below. The impellers 222 and 224 may be formed in accordance with well-known design techniques, depending on the pressure, velocity and flow characteristics desired. For example, as shown in FIGS. 3 and 4, the inlet impeller 222 may include a four blade design and the discharge impeller 224 may include a five blade design. Alternatively, the inlet impeller 222 could include three blades, and the discharge impeller 224 could include four, six or seven blades. The common shaft 226 is rotatably coupled to the impellers 222 and 224 by a press-fit and bonded connection. A plastic spacer sleeve 228 is mounted on the drive shaft 226 between the impellers. The drive shaft 226 includes a forward end rotatably mounted in the bearing 214 and shaft receptacle 210, and a rearward end. A shim spacer 230 of conventional design is disposed between the forward end of the impeller 222 and the bearing 214. In the drive shaft 226 itself, there is provided a rearward cavity 246 adapted to receive a motor output shaft, as described in more detail below.

The secondary impeller 224 is disposed immediately forward of the exhaust formed by the vents 148 in the vacuum chamber housing 130. The rearward end of the drive shaft 226 is rotatably mounted in a motor support 240 made from durable plastic material. The motor support 240 is preferably slideably engaged in the rearward end of the pump chamber housing 130, and includes an annular stop tab 242 that abuts the pump chamber housing rear face 136. The motor support 240 is also press-fit and bonded into the rearward end section 120 such that the tab 242 also abuts that barrel. Thus, it will be appreciated that the rearward end section 120 and the pump chamber housing 130 are joined together by mutual engagement with the motor support 240. In addition, although the rearward end section 120 is permanently bonded to the motor support 240, these components could be slideably mounted if periodic disassembly was desired. Alternatively, these components, as well as the vacuum chamber housing 130 and motor support 240, could be joined by a threaded arrangement. The motor support 242 has a conical forward end 244 which serves to direct a gas stream provided from the two stage impeller assembly through the exhaust 148. The rearward end of the drive shaft 226 is disposed within a cylindrical guide aperture 246 formed at the axial center of the cone 244. There is disposed within the interior of the rearward end of the drive shaft 226, a plastic coupling sleeve 250. The coupling sleeve 250 is coupled to the drive shaft 226 by means of a key arrangement in which a pair of parallel opposing side walls are formed in the otherwise cylindrical areas of mutual engagement.

Removably mounted within the motor support 240 is an electric D/C drive motor 260. The drive motor 260 includes an output shaft 262 extending from a shoulder 264. The output shaft 262 is rotatably connected to the coupling sleeve 250 by means of a press-fit and bonded arrangement. To stabilize the drive shaft 226 and the components mounted thereon relative to the drive motor shaft 262, a steel preloading spring 266 is disposed in the cavity 232 of the drive shaft 226. The spring 266 is biased between the forward end of the cavity 232 and the forward end of the motor output shaft 262. Alternatively, the length of the cavity 232 could be reduced and silicon material could be placed in the reduced space between the forward end of the cavity 232 and the motor output shaft 262. Disposed rearwardly of the drive motor 260 is an electrical switch 270 mounted by bonding or other suitable attachment arrangements against a generally disc-shaped housing partition 272 mounted in the rearward case section 120. The switch 270 is mounted laterally with respect to the case section 120 and includes a switch handle 274 extending laterally through an aperture 275 in the case section 120. The button 274 is mounted on a plunger 276 and is outwardly biased by a spring 278. The switch 270 is electrically connected to the drive motor 260, and also to a battery arrangement 280 disposed rearwardly of the housing partition 272.

As shown in FIG. 2B, the battery arrangement 280 includes at least one rechargeable battery, preferably of the nickel-cadmium variety, capable of generating between about three and nine volts. If more than one battery is used, the batties may be shrink-wrapped together for convenience. The batteries 280 are electrically connected to the drive motor 260 through the switch 270, such that the switch controls the electric current from the batteries to the drive motor. The battery arrangement 280 is supported at its rearward end by a plastic battery cap 290 which is preferably engaged in a press-fit and bonded arrangement with the rearward end of the case section 120. Alternatively, the battery cap could be slideably or threadably mounted for removable connection to the rearward section 120. The battery cap 290 includes a forward tubular portion 292 adapted for press-fit mounting into the rearward end of the case section 120. The battery cap 290 further includes an annular shoulder 294 that abuts the rear face of the case section 120. The battery cap 290 also includes an inner cylindrical surface 296 sized to receive the rearmost battery of the battery arrangement 280. The cylindrical surface 296 terminates at a rearward end wall 298. Disposed in the end wall 298 are a pair of metal contacts 300 which extend to corresponding positive and negative terminals of the battery arrangement 280. To accommodate the contact terminals 300, the end wall 298 is provided with a pair of wells 302 connected by ports 304 to the interior recess of the battery cap 290. The contacts 300 are fixedly supported in the wells 302 and extend forwardly through the ports 304 for connection to the battery arrangement 280. As shown, the battery cap 290 is configured for engagement with a recharging unit described below. Thus, the battery cap end wall 298 includes a frusto-conical surface 306 extending forwardly and outwardly at the sides thereof.

Referring now to FIG. 2A, the vacuum housing 130 has disposed therein a vacuum pulsing system 310 which provides a pulsed vacuum at the mouthpiece 150. The vacuum pulsing system 310 includes the annular groove 142 and passage 144 formed in the pump chamber housing 130. The annular passage 144 and interior vent chamber 146 are covered by a vent louver 312 extending around the periphery of the pump housing 130, over the annular groove 142. The interior vent chamber is formed by a forward wall section 314 that extends to the annular face 140. The interior vent chamber 146 is further formed by a rearward wall section 316 having an interior frustoconical surface 318 tapering inwardly in a rearward direction in adjacent relationship with the inwardly tapering impeller 222. The rearward wall section 316 further includes an annular valve seat 320. There is disposed rearwardly adjacent the annular valve seat 320 a generally ring-shaped, plastic valve 322. The valve is illustrated in a closed position in FIG. 2A using solid line representation and in an open position using phantom line representation. The valve 322 is slideably mounted with respect to the valve seat 320 by means of a plurality of steel valve actuator pins 324 which extend forwardly into corresponding pin receptacles 326 formed in the annular valve seat 320 of the rearward wall section 316 of the pump chamber housing 130. In order to provide an air passage from the interior vent chamber 146 to the interior of the pump housing 130 when the valve 322 is displaced rearwardly there are provided more pin receptacles 326 than there are actuator pins 324. For example, there may be provided three pins 324 and sixteen receptacles 329. FIG. 2A shows receptacles 326 both with and without an actuator pin 324.

Figure 6:
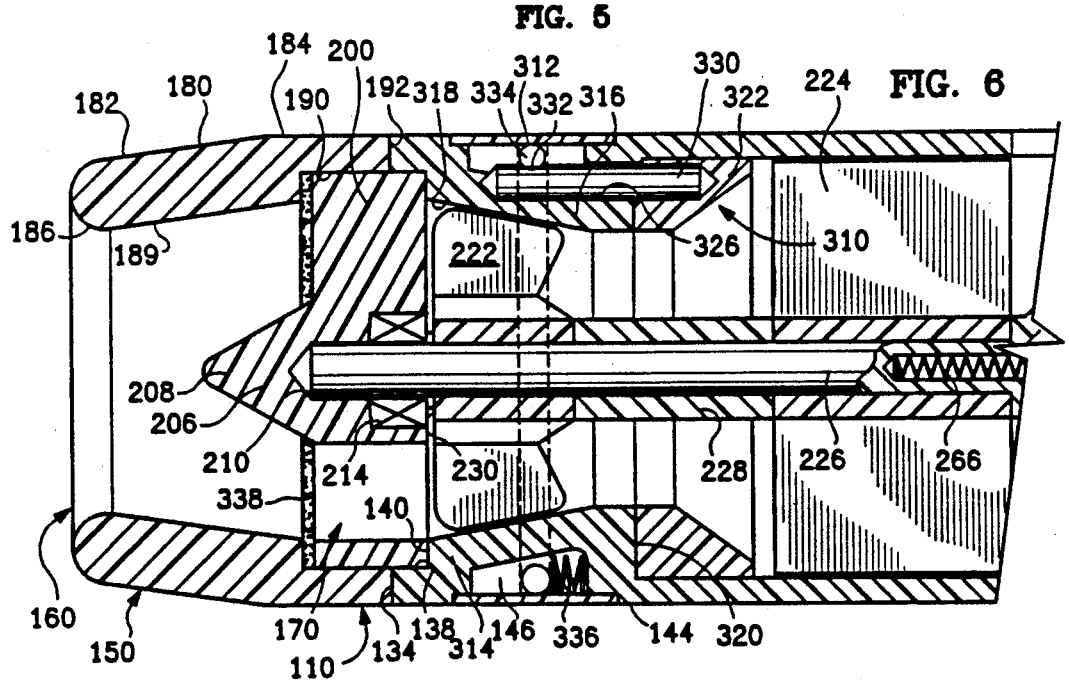
FIG. 6 is a partial cross-sectional side view of a modification of the lung purger and ventilator system of FIG. 2A.

The valve 322 is resiliently biased in a preferred manner under low pressure conditions by the magnetic attraction of the pins 324 toward an annular magnet 328 disposed in the interior vent chamber 146. When the pressure inside the vacuum chamber housing 130 exceeds the closing force provided by the magnet 328, the valve 322 is displaced rearwardly and the vacuum chamber housing 130 is vented through the receptacles 326, to the interior vent chamber 146, to the annular passage 144, and thence through the array of vents provided by the louvers 312, to purge the vacuum chamber housing 130 of its vacuum. Alternatively, as shown in FIG. 6, the valve 322 may be slideably mounted to the valve seat 320 by pins 330 extending through the pin receptacles 326. The pins 330 include a lateral notch 332 which engages and supports a ring 334 extending around the annular passage 144. The ring 334 is free to slide with the pins 330 as the valve 322 displaces. The ring 334 is biased forwardly, however, by springs 336. The springs 336 thus provide a valve actuator closing force that closes the valve 322 under low pressure conditions.

Figure 5:
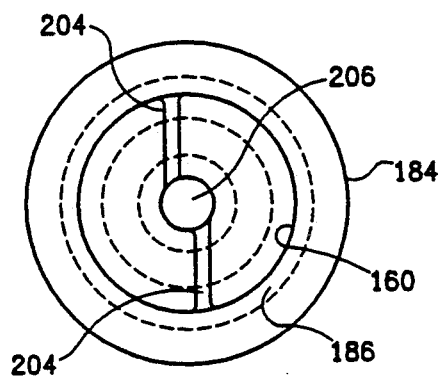
FIG. 5 is an end view of the forward end of the lung purger and ventilator system of FIG. 2A.

As shown in FIGS. 2A and 5, the interior of the apparatus is aerodynamically formed to provide an annular fluid passage. A venturi effect is created resulting from the gas stream flow from the central inlet 160 to the peripheral exhaust 148. Preferably, the rotational output speed of the motor, the design of the impeller blades, and the cross-sectional interior flow area, are selected to optimally generate a fluid velocity which is about four times normal exhale velocity and slightly above the velocity of exhale during peak exercise activity. Thus, the lung purger apparatus serves to exchange the volume of air in the lungs at an accelerated rate than would otherwise be achieved through ordinary breathing. This rapid exchange of air serves to expel various damaging particulates ingested in the lungs and prevents them from permanently settling on the lung tissue. In addition, the generated vacuum pressure causes the valve 322 to periodically open, thus resulting in a vacuum pulsing effect. This pulating action should assist in freeing and removing contaminants that have contacted the lung surface.

Thus, regular use of the apparatus will increase the number of total volume air changes that the individual's pulmonary system would normally experience. Individuals who do not regularly exercise or otherwise increase their respiratory rate can benefit from the enhanced air exchange provided and thereby reduce the level of contaminants allowed to settle on the lung tissue. At the same time, despite the substantially increased air withdrawal velocity provided by the device, the generated vacuum will not interfere with normal breathing due to the fact that air may still be inhaled during use through the nose. Thus, hyperventilation and depletion of oxygen in the pulmonary system is avoided, rendering the device completely safe for an extended use.

As shown in FIG. 14, to operate the system, the user grasps the rearward section 120 of the case 100 in one hand, inserts the mouthpiece 150 in the mouth and activates the switch button 274. A vacuum pulsing follows which does not interfere with normal breathing but which causes an enhanced withdrawal of contaminants from within the lungs. The vacuum pulsing system 310 may be designed to provide vacuum pulsing at selected time intervals. For example, vacuum purging could be programmed to occur at approximately six to ten second intervals and to last about one second before the valve 322 again closes. The system may be operated for as long as desired to effect an enhanced exchange of air. If desired, a filter 338 may be removably mounted over the hub 206 of the forward bearing support 200, and retained between the support 200 and the annular face 188 of the forward end section 110. The filter 338 helps prevent contaminated air from recirculating from the exhaust 148 to the user's respiratory system through the nose. The filter 330 may be changed as desired by separating the forward end section 110 from the bearing support 200.

Figure 7:
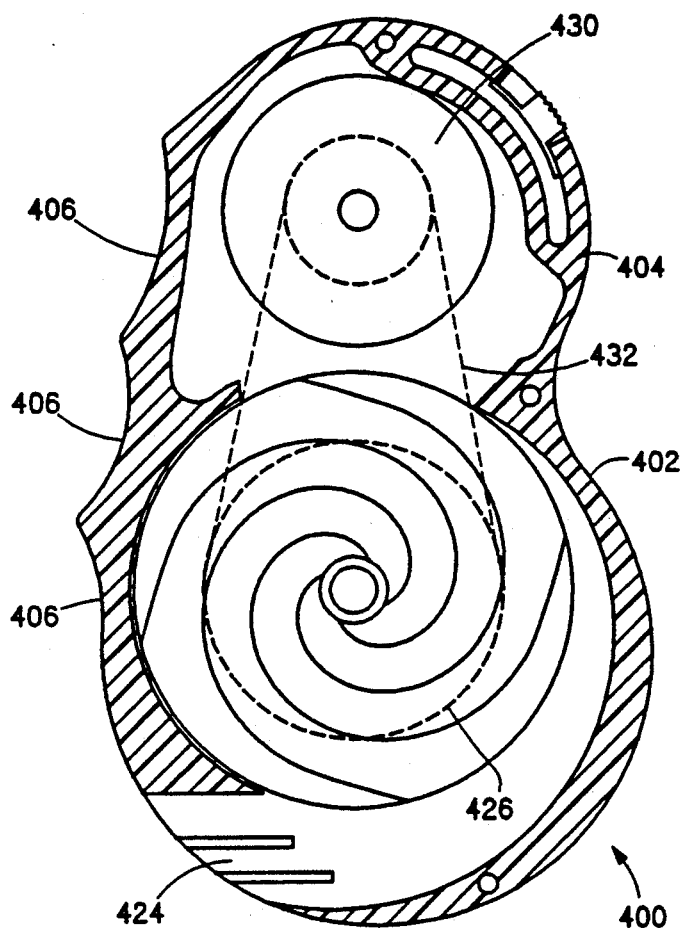
FIG. 7 is a cross-sectional plan view of a lung purger and ventilator system constructed in accordance with a still further aspect of the present invention.
Figure 8:
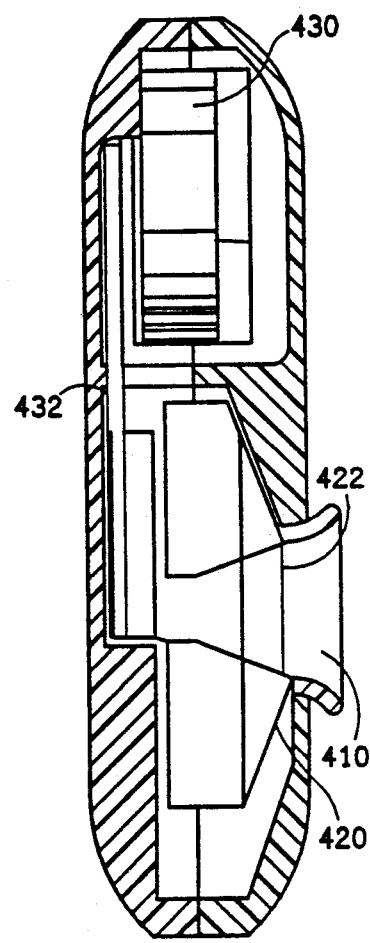
FIG. 8 is a cross-sectional side view of the lung purger and ventilator system of FIG. 7.
Figure 9:
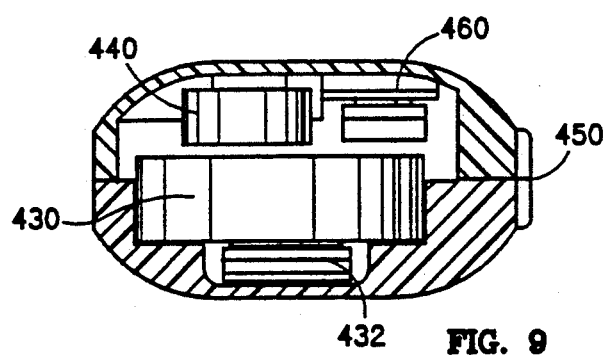
FIG. 9 is a cross-sectional end view of the lung purger and ventilator system of FIG. 7.

Referring now to FIGS. 7-9, a lung purging and ventilation system constructed in accordance with a further aspect of the invention includes a case 400 forming a first chamber 402 and a second chamber 404. The case 400 includes a series of finger grooves 406 to facilitate gripping when the device is held in the palm of the hand. The first chamber 402 of the case 400 has a mouthpiece 410 extending to a pump 420, including an inlet 422, and outlet 424 and an impeller 426, which is rotatably mounted in the chamber 402. The pump 420 acts to draw a gas stream through the mouthpiece 410 and the pump inlet 422 and dispenses the gas stream through the vented pump exhaust 424 formed in the side of the case 400. There is disposed in the second chamber 404 a motor 430 connected by a belt drive 432 to the pump impeller 426. The motor 430 is powered by a battery 440 which is also disposed in the second chamber 404 of the case 400. There is further disposed in the chamber 404 a switch 450 that controls the flow of electric current from the battery 440 to the drive motor 430. In addition, there is disposed in the chamber 404 a pulsing circuit 460 which periodically interrupts the flow of current from the battery 440 to the motor 430 to thereby control the pump to generate a pulsed vacuum.

The pulsing circuit 460 is illustrated in detail in FIG. 9. Although there are many alternative circuits which could be used to provide a timing function, a preferred pulsing circuit includes an integrated circuit timing module 462 and external register capacitor networks operating in a monostable (one-shot) mode with frequency and duty cycle controlled by the values of the resistor capacitor networks. The timing module 462 is conventional in nature and includes a starting circuit, voltage comparison and other functions needed for a complete timing circuit. A preferred timing module is available from Motorola Corporation under the designation MC1455. The module 462 includes a pair of comparators, one for pulse duration and the other for dwell. There is also included a flip-flop and a digital output. In the module 462, pin 1 is a ground connection, pin 2 is a connection to a trigger comparator, pin 3 is a digital output connection, pin 4 is a flip-flop reset connection, pin 5 is a control voltage connection, pin 6 is a threshold comparator connection, pin 7 is a discharge transistor connection, and pin 8 is a connection to the supply voltage Vcc, which is preferably about six volts DC. In the monostable mode, the resistor capacitor networks $R_1C_1$ and $R_2C_2$ control timing. When the input voltage provided through the RC network of resistor $R_1$ and capacitor $C_1$ to the trigger comparator terminal 2 falls below $\frac{1}{3}$ Vcc, an internal trigger comparator triggers an internal flip-flop in the module 462 so that its output is set low. This turns an internal capacitor discharge transistor "off" at terminal 7 and drives the digital output at terminal 3 to a high state. The motor 430 is thereby provided with an operating voltage to drive the pump 420. This condition allows the capacitor $C_2$ to charge at a rate set by the RC time constant of the resistor $R_2$ and capacitor $C_2$ network. When the capacitor $C_2$ voltage reaches $\frac{2}{3}$ Vcc, an internal threshold comparator connected to terminal 6 resets the flip-flop. This action causes the capacitor $C_2$ to discharge and resets the digital output to the low state. The voltage supply to the motor 430 is interrupted and the pump 420 is turned off. The trigger voltage at terminal 2, and hence the time delay until the next high level output from the terminal 3 is determined by the discharge rate of the capacitor $C_1$ and resistor $R_1$. In a preferred embodiment, the values of resistor $R_1$, capacitor $C_1$, resistor $R_2$ and capacitor $C_2$ are selected for a six VDC input voltage Vcc to provide a fifteen second high level output from the output terminal 3 followed by a one second low level output. It will be understood and appreciated that many other pulse/dwell combinations could be effectively utilized in order to achieve desired results.

Referring now to FIG. 11, the lung purging and ventilating system of FIGS. 2A and 2B may be provided with a cap 600 adapted to fit over the case 100 to cover the inlet 160 and the exhaust 148. There may be further provided a recharging unit 700 for recharging the rechargeable batteries 280 when the device is not in use. The cap 600 includes a plurality of longitudinally extending depressions 610 in a otherwise generally tubular body 620. A clip 630 may be provided for conveniently affixing the case 100 and cap 600 in a shirt pocket, or to an automobile sun visor or other structure.

The recharging unit 700 is conventional in nature and functions in accordance with the circuit diagram shown in FIG. 12. As shown, a 115-volt A/C line input is provided to a circuit including step-down transformer T, a full wave rectifier D, a resistor R, and fuses $F_1$ and $F_2$, to produce a six-volt D/C output at a pair of contacts which electrically engage the contacts of the battery cap previously described. The recharger circuit is conveniently provided in an integrated circuit module 710 of conventional design. The module 710 is affixed to the inside of the recharger base housing 720. An outlet cord 730 provides connection to a 115-volt A/C line source. The module 710 is mounted to the inside of the housing 720 by bonding or other conventional attachment arrangements. The module 720 is electrically connected to a pair of contact rings 730 and 740, which are disposed within a receptacle 750. As also shown in FIG. 13, the receptacle 750 is sized and configured to receive and matingly support the end cap 290 of the lung purger and ventilator system of FIGS. 2A and 2B.

Figure 15:
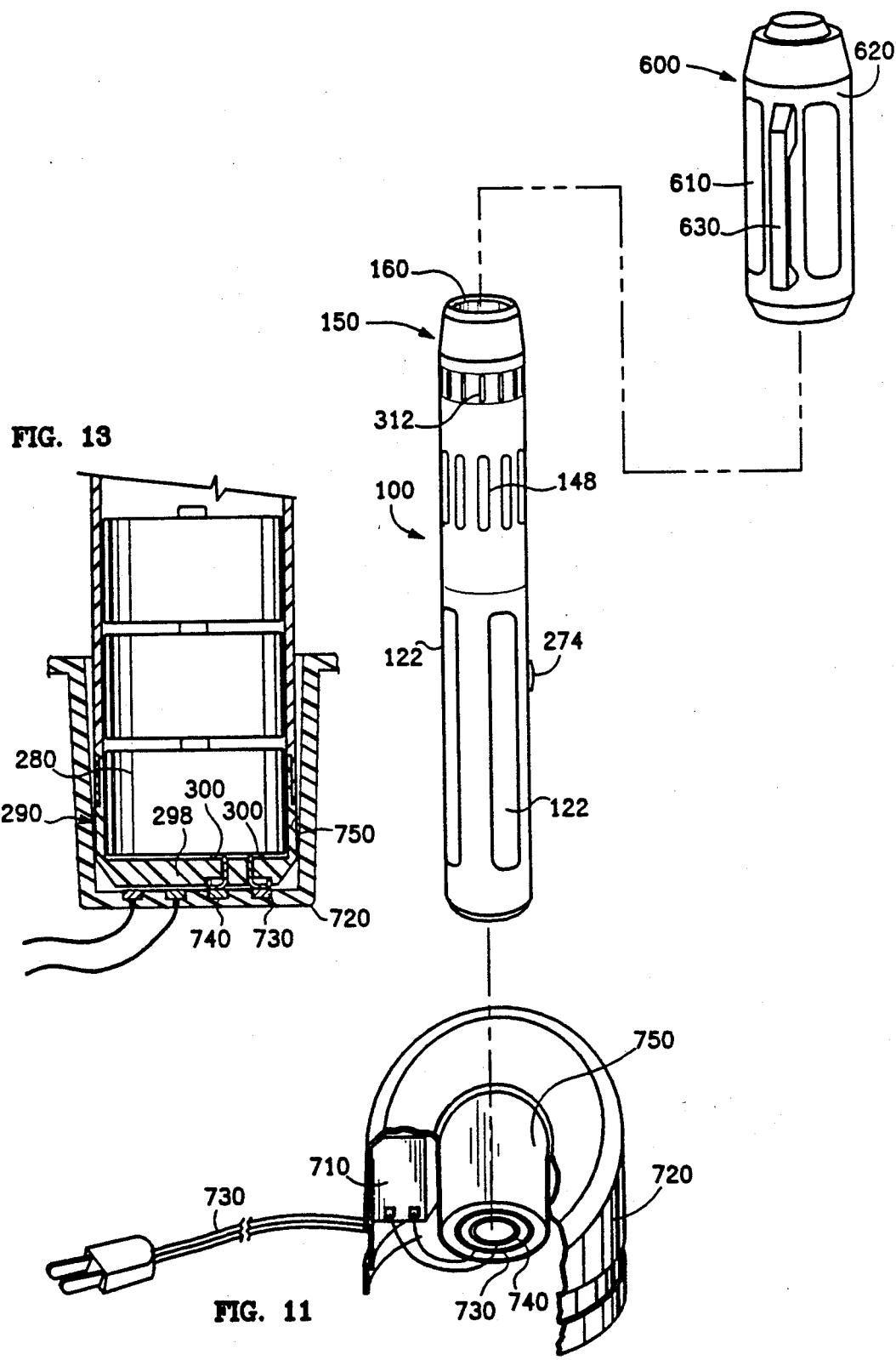
FIG. 15 is a diagrammatic illustration of a lung purger and ventilator system constructed in accordance with described aspects of the present invention.

Referring now to FIG. 15, the lung purger and ventilator system of FIGS. 2A and 2B is illustrated diagrammatically as a system 800, and is shown in conjunction with an individual 802 whose pulmonary system is illustrated diagrammatically at 804. The lung purger 800 includes a mouthpiece 806 providing an air inlet to a two-stage pump 808 including a primary impeller 810 and a secondary impeller 812 mounted on a common shaft 814. The pump 808 is drivably connected to a motor 816 through a drive shaft coupling 818. The motor 818 is powered through a battery pack 820 through the control of a finger operable switch 822. The mouthpiece, vacuum pump, motor, switch and batteries are all arranged in a portable assembly 824 which is generally cylindrical in nature and sized and configured to be held in the palm of an individual's hand. The lung purger and ventilator system 800 further includes a vacuum purging system disposed in the portable assembly 824, including a pair of purge valves 826 disposed forwardly of the secondary impeller 812. The purge valves 826 may be constructed in accordance with the design of vacuum pulsing system 310. In addition, it will be understood and appreciated that many other mechanical or electro-mechanical purge systems could be used. For example, spring-biased poppet valves or electrical servo-mechanisms could be used as purge valves. The purge valves 826 periodically open as a predetermined pressure is generated by the pump 808. The portable assembly 824 further includes a peripheral array of vents providing an exhaust 828 from the pump 808. The individual operates the lung purger and ventilator system 800 by grasping the portable assembly 824 in the palm of the individual's hand. For that purpose, the portable assembly 924 is conveniently provided with a handgrip adapted to be grasped by the individual. The mouthpiece 806 is placed in the individual's mouth and the switch 822 is activated to generate a pulsed vacuum at the mouthpiece 806. This serves to generate a high velocity purging of air in the pulmonary system 804 such that contaminants residing therein are removed.

Figure 16:
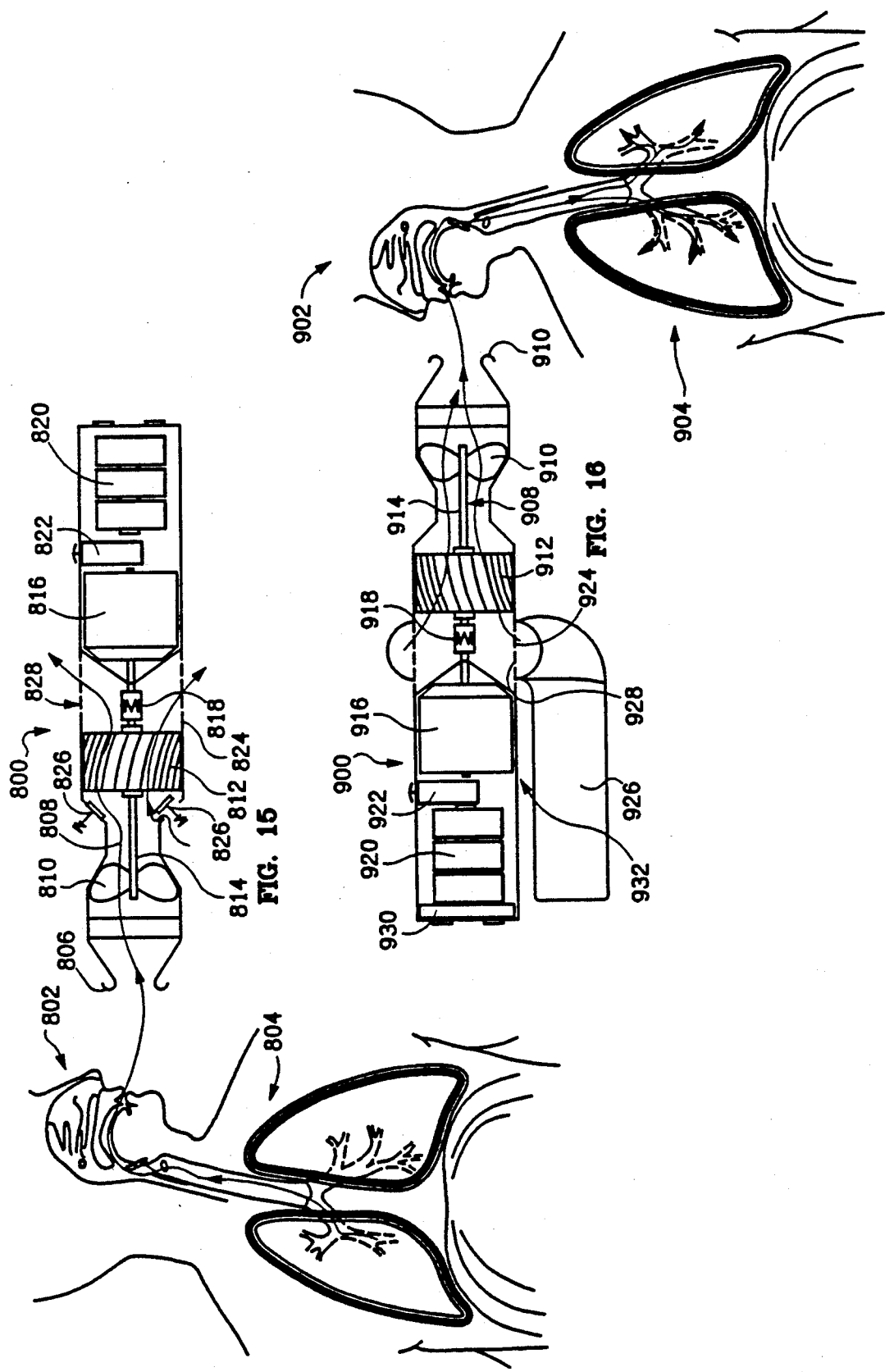
FIG. 16 is a diagrammatic illustration of a lung purger and ventilator system constructed in accordance with a still further aspect of the present invention.

Referring now to FIG. 16, a lung purger and ventilator system 900 adapted for the introduction of medicament into an individual 902 whose pulmonary system is shown diagrammatically at 904, will now be described. The system 900 is generally similar to the system 800 described above and includes a mouthpiece 906 and a two-stage pump 908 having a primary impeller 910 and a secondary impeller 912 mounted on a common shaft 914. The pump 908 is driven by a motor 916 connected to the pump by a coupling 918. The motor 916 is in turn powered by a battery power source 920 which is controlled by a switch 922. Unlike the system 800 described above, the system 900 operates in a reverse mode to exhaust air into the pulmonary system 904 as shown by the arrows in FIG. 16. In this mode of operation, a peripheral array of vents 924 serves as an inlet and the mouthpiece 906 serves as an outlet for the pump 908. The inhaler uses the reverse action of the pump to inject air into the lungs. In addition, a disposable cartridge 926 having an angular outlet 928 can be slid over the vent openings 924. The cartridge 926 contains medicament to be inhaled. When operated by the individual 902, the air containing the medicament vapors will be injected into the lungs by the pump 908. In addition, a pulsing action may be provided by a pulsing circuit 930 disposed adjacent the battery power source 920. The pulsing circuit 930 may be constructed in accordance with the circuit 460 described above with appropriate pulse/dwell values being selected. The mouthpiece 906, the pump 908, the motor 916, the switch 922, the battery power source 920 and the timing circuit 930 are all arranged in a portable assembly 932 which is sized and configured to be held in the palm of an individual's hand. The medicament container 926 is sized such that the medicament container 926 and portable assembly 932 can be conveniently held in one hand.

Figure 17:
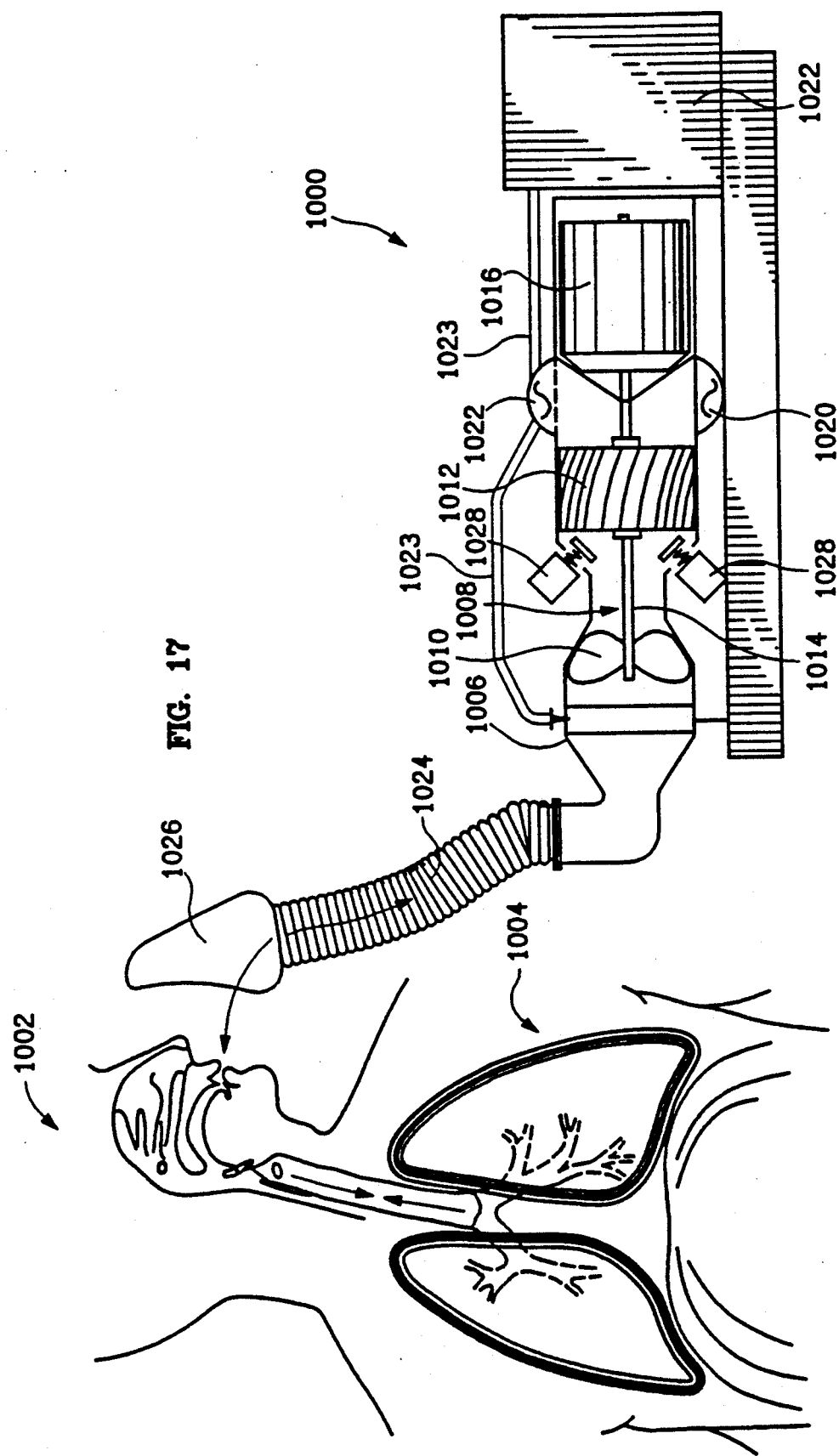
FIG. 17 is a diagrammatic illustration of a lung purger and ventilator system constructed in accordance with a still further aspect of the present invention.

Referring now to FIG. 17, a lung purger and ventilator system 1000 may be utilized by an individual 1002 whose pulmonary system is illustrated diagrammatically at 1004. In the arrangement of FIG. 17, the individual may have lung congestion such as may commonly develop after surgery or other treatments. Thus, the lung purger and ventilator system 1000 is provided with the dual capability to inject air/vapor into the lungs and also to provide a pulsating suction action to clear the lungs of the congestion. The system 1000 is similar in most respects to the systems 800 and 900. Thus, the system 1000 includes a manifold 1006 and a pump 1008 including a primary impeller 1010 and a secondary impeller 1012 mounted on a common shaft 1014. The pump 1008 is driven by a motor 1016 through a coupling (not shown) of conventional design. The motor 1016 is driven by a power source (not shown) of conventional design, which may be portable or non-portable. The manifold 1006, pump 1008 and motor 1016 are mounted in an assembly 1018 which is itself supported on a platform 1019. The assembly 1018 includes a peripheral array of exhaust vents 1020 which is covered by a one-way flow screen 1022. The flow screen 1022 allows air to pass from the interior of the assembly 1018 to the exterior thereof, but will not allow the air to flow in a reverse direction through the vent system 1020. The manifold 1006 is further connected to a source of vaporized air 1022 also mounted on the platform 1019, through an inlet line 1023. The manifold 1006 is further connected to a vent tube 1024 extending to a mask 1026 sized and configured to fit over the nose and mouth of the individual 1002. The system 1000 is further provided with a pair of servo-control pulse valves 1028. The pulse valves 1028 may be adjusted to periodically open to purge air generated by the pump 1008 from the system. The motor 1016 is provided with a reversible and variable speed control so that air can be selectively injected into the individual's pulmonary system 1004 and thereafter purged in accordance with a pulsed mode of operation determined by the pulse valves 1028. Thus, the system 1000 may first be operated in a pulse injection mode for a selected period of time to inject vaporized air through the mask 1026 and to the pulmonary system 1004. Thereafter, the system 1000 is operated to apply a pulsed vacuum to the individual's pulmonary system to remove by pulsating suction action contaminants loosened during the pulse injection phase.

While I have described several preferred embodiments of my Portable Lung Purger and Ventilator System, it should be understood that modifications and adaptations thereof will occur to persons skilled in the art. For example, as shown from the Figures, many alternative assembly configurations and design arrangements could be employed to provide a functional system embodying the inventive concepts herein. Therefore, the protection afforded the invention should not be limited except in accordance with the spirit of the following claims and the equivalents thereof.

I claim:

1. A portable lung purger and ventilator system for exhausting airborne contaminants from the lungs, comprising:
    a mouthpiece sized and configured for placement in an individual's mouth, the mouthpiece having an inlet for receiving a gas stream and an outlet for transferring a gas stream received through the inlet;
    a vacuum pump having an inlet in fluid communication with the mouthpiece for receiving a gas stream, and an outlet for exhausting a gas stream received through the pump inlet, the vacuum pump generating a vacuum at the mouthpiece;
    a drive operatively connected with the vacuum pump for providing motive power thereto;
    a switch operatively connected with the drive for controlling operation thereof;
    a portable power source operatively connected with the drive for providing power thereto; and
    the mouthpiece, vacuum pump, drive, switch and power source being arranged in a portable assembly.

2. The system of claim 1 further including a pressure relief valve for purging the vacuum generated by said vacuum pump when the vacuum reaches a predetermined level.

3. The system of claim 1 further including a vacuum pulsing system for periodically reducing the vacuum generated by said vacuum pump.

4. The system of claim 3 wherein said pulsing system includes a pressure relief valve sized and configured to periodically open when the vacuum generated by said vacuum pump reaches a predetermined level.

5. The system of claim 3 wherein said pulsing system includes means for controlling said power source to provide an electrical pulse to said drive.

6. The system of claim 4 wherein said pulsing system includes a slide valve and louver system.

7. The system of claim 1 further including a gas filter for filtering particulate matter transported with a gas stream through said mouthpiece.

8. The system of claim 1 wherein said vacuum pump includes first and second impeller stages.

9. The system of claim 1 wherein said portable power source includes rechargeable batteries.

10. A method for purging airborne contaminants from the lungs, comprising the steps of:
    grasping in one or both of an individual's hands a lung purging apparatus having a housing including a mouthpiece and a hand gripping surface area sized and configured to be supported in an individual's hand, the apparatus further having a vacuum airflow system extending from the mouthpiece to an exhaust, a drive system for driving the vacuum airflow system to generate a vacuum at the mouthpiece and a power system for controllably powering the drive system;
    placing the mouthpiece at the individual's mouth;

activating the lung purging apparatus to generate a vacuum at the mouthpiece; and continuing application of the vacuum for a selected time period.

11. The method of claim 10 wherein the lung purging apparatus includes vacuum pulsing means for periodically purging the vacuum generated by the vacuum pump.

12. A portable lung purger and ventilator system for exhausting airborne contaminants from the lungs, comprising:

a case sized and configured to be held in the palm of an individual's hand, having a hand grip adapted to be grasped by an individual and a mouthpiece sized and configured for placement at an individual's mouth, said mouthpiece having an inlet for receiving a gas stream from the individual's mouth and an outlet for transferring a gas stream received through the inlet;

a vacuum pump disposed in said case having an inlet in fluid communication with said mouthpiece for receiving a gas stream and an outlet for exhausting a gas stream received through said pump inlet;

a drive disposed in said case operatively connected with said vacuum pump for providing motive power thereto;

a switch disposed in said case operatively connected with said drive for controlling operation thereof; and a portable power source disposed in said case operatively connected with said drive for providing power thereto.

13. The system of claim 12 wherein said case is generally cylindrical and said mouthpiece, vacuum pump, drive and power source are arranged generally sequentially within said case.

14. The system of claim 12 wherein said mouthpiece forms an extension at one end of said case and includes a generally tapered end portion for comfortably engaging an individual's mouth.

15. The system of claim 12 wherein said pump outlet includes a peripheral array of exhaust ports in said case.

16. The system of claim 12 further including a purge valve having a plurality of peripheral openings in said case, a slideable valve element and means for biasing said valve to a closed position.

17. The system of claim 12 wherein said case is generally kidney shaped and includes a first chamber having disposed therein said pump and mouthpiece and a second chamber having disposed therein said drive, power source and switch.

18. The system of claim 12 further including means for reversibly driving said vacuum pump, and a fluid source in fluid communication with said mouthpiece for directing fluid disposed in said fluid source into a gas stream exiting said mouthpiece when said vacuum pump is reversed.

19. The system of claim 12 further including means for injecting pulsed humidified air from said mouthpiece.

20. A portable lung purging apparatus for removing airborne contaminants from the lungs, comprising:

a generally tubular housing sized to be held in the palm of an individual's hand, having a gripping surface adjacent a rearward end thereof and a mouthpiece at a forward end thereof, said mouthpiece having an inlet for receiving a gas stream from an individual's mouth, an outlet for dispelling a gas stream received through said inlet and a generally tapered outer surface portion extending between said inlet and outlet;

a bearing support disposed in said case rearwardly adjacent said mouthpiece, having a bearing disposed along an approximate centerline of said case;

a vacuum pump disposed in said case rearwardly adjacent said bearing support having first and second impellers mounted on a common pump shaft, said shaft having a forward end mounted in said bearing support and a rearward end;

an gas stream exhaust disposed in said case rearwardly adjacent said pump having an array of exhaust ports arranged around the periphery of said case;

a drive motor disposed in said case rearwardly adjacent said pump having an output shaft rotatably coupled with the second end of said pump shaft;

a battery arrangement disposed in said case rearwardly adjacent and electrically connected with said drive motor;

a switch disposed in said case adjacent said battery arrangement and extending through the periphery of said case for actuation by a user; and a vacuum pulsing system including an array of vents disposed in the periphery of said case between said bearing support and said gas stream exhaust, at least one passage extending from said vents to a generally annular valve seat disposed at an interior portion of said case rearwardly adjacent said first pump impeller, and a generally ring-shaped valve actuator slideably mounted in said case and biased against said annular valve seat, said valve actuator being biased to close against said valve seat until a selected vacuum is generated by said vacuum pump causing said valve actuator to open.

* * * * *